United States Patent
Fishell et al.

(10) Patent No.: US 10,682,424 B2
(45) Date of Patent: Jun. 16, 2020

(54) COMPOSITIONS AND METHOD FOR REDUCING SEIZURES

(71) Applicant: New York University, New York, NY (US)

(72) Inventors: Gordon Fishell, Larchmont, NY (US); Jordane Dimidschstein, Seraing (BE)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/561,547

(22) PCT Filed: Mar. 31, 2016

(86) PCT No.: PCT/US2016/025283
§ 371 (c)(1),
(2) Date: Sep. 26, 2017

(87) PCT Pub. No.: WO2016/161124
PCT Pub. Date: Oct. 6, 2016

(65) Prior Publication Data
US 2018/0078658 A1 Mar. 22, 2018

Related U.S. Application Data

(60) Provisional application No. 62/140,631, filed on Mar. 31, 2015.

(51) Int. Cl.
| | | |
|---|---|---|
| *A61K 39/002* | (2006.01) | |
| *A61K 48/00* | (2006.01) | |
| *C12N 15/86* | (2006.01) | |
| *C07K 14/705* | (2006.01) | |
| *A61K 38/17* | (2006.01) | |
| *C07K 14/72* | (2006.01) | |
| *C12N 7/00* | (2006.01) | |
| *A61K 38/00* | (2006.01) | |

(52) U.S. Cl.
CPC ...... *A61K 48/0066* (2013.01); *A61K 38/1796* (2013.01); *C07K 14/705* (2013.01); *C07K 14/723* (2013.01); *C12N 7/00* (2013.01); *C12N 15/86* (2013.01); *A61K 38/00* (2013.01); *C12N 2750/14121* (2013.01); *C12N 2750/14143* (2013.01); *C12N 2830/008* (2013.01); *C12N 2830/30* (2013.01); *C12N 2830/42* (2013.01); *C12N 2830/48* (2013.01); *C12N 2830/50* (2013.01)

(58) Field of Classification Search
None
See application file for complete search history.

(56) References Cited

PUBLICATIONS

Alexander et al Remote Control of Neuronal Activity in Transgenic Mice Expressing Evolved G Protein-Coupled ReceptorsNeuron 63, 27-39, Jul. 16, 2009; pp. 27-38.*
MacLaren et al., Clozapine-n-oxide administration produces behavioral effects in Long-Evans rats—implications for designing DREADD experiments eNeuro 2016; pp. 1-32.*
Zerucha et al., A Highly Conserved Enhancer in the DIx5/DIx6 Intergenic Region is the Site of Cross-Regulatory Interactions between DIx Genes in the Embryonic Forebrain the Journal of Neuroscience, Jan. 15, 2000, 20(2):709-721.*
Yi, Feng, et al., Muscarinic excitation of parvalbumin-positive interneurons contributes to the severity of pilocarpine-nduced seizures, Epilepsia, Feb. 2015, vol. 56, No. 2, pp. 297-309.
Ghanem, N., et al., Distinct cis-Regulatory Elements from the DIx1/DIx2 Locus Mark Different Progenitor Dell Populations in the Ganglionic Eminences and Different Subtypes of Adult Cortical Intemeurons, The Journal of Neuroscience, May 9, 2007, vol. 27, No. 19, pp. 5012-5022.
Delzor, A., et al., Restricted Transgene Expression in the Brain with Cell-Type Specific Neuronal Promoters, Human Gene Therapy Methods, Aug. 2012, vol. 23, pp. 242-254.
Stuhmer, T., et al., Expression from a DIx Gene Enhancer Marks Adult Mouse Cortical GABAergic Neurons, Cerebral Cortex, Jan. 2002, vol. 12, pp. 75-85.
Urban, D.J., et al., DREADDs (Designer Receptors Exclusively Activated by Designer Drugs): Chemogenetic Tools with Therapeutic Utility, Annu. Re. Pharmacol. Toxicol., Sep. 25, 2014, vol. 55, pp. 15.1-15.19.
Krook-Magnuson, E., et al., On-demand optogenetic control of spontaneous seizures in temporal lobe epilepsy, Jan. 22, 2013, Nature Communications, vol. 4, No. 1376, 8 pages.

* cited by examiner

Primary Examiner — Maria G Leavitt
(74) Attorney, Agent, or Firm — Hodgson Russ LLP

(57) ABSTRACT

Provided are compositions and methods for prophylaxis and/or therapy of disorders that involve seizures. The compositions and methods relate to a recombinant adeno-associated virus (rAAV) comprising a I56i enhancer sequence, and a sequence encoding hM3Dq modified muscarinic receptor (Gq-DREADD). The method includes introducing the rAAV into interneurons of an individual such that Gq-DREADD is expressed in interneurons of the individual. The method can further comprise administering to the individual an agonist of the Gq-DREADD, such for reducing or preventing seizures.

5 Claims, 4 Drawing Sheets
Specification includes a Sequence Listing.

COMPOSITIONS AND METHOD FOR REDUCING SEIZURES

CROSS REFERENCE TO RELATED APPLICATIONS

This application claims priority to U.S. provisional patent application No. 62/140,631, filed Mar. 31, 2015, the disclosure of which is incorporated herein by reference.

STATEMENT REGARDING FEDERALLY SPONSORED RESEARCH

This invention was made with government support under grant no. R01MH071679 and P01NS074972 awarded by National Institutes of Health. The government has certain rights in the invention.

FIELD

The present disclosure relates generally to prophylaxis and/or therapy of seizures and more specifically to use of modified viral vectors for localized suppression of neuronal excitability at seizure foci.

BACKGROUND OF THE DISCLOSURE

Epilepsy is a devastating neurological disorder that is characterized by recurrent seizures, often of an unknown cause, which affects approximately 1% of the world's population. A large fraction of epileptic patients suffers from seizures that are refractory to anti-epileptic drugs (AEDs). In the case of intractable temporal lobe epilepsy, surgical resection helps to reduce the seizures but the rate of complete remission is low (<50%) and is not ideal because cognitive comorbidities may arise from removing brain tissue. As a result, a significant fraction of individuals remain medically intractable. The underlying cause of epilepsy is believed to arise from a defect in the excitation-inhibition (E/I) balance of cortical circuits. Forebrain GABAergic interneurons are the primary source of inhibition in the telencephalon and various lines of evidence indicate their importance in epilepsy. There is an ongoing need for new compositions and methods for modulating that activity of the GABAergic interneurons to provide prophylaxis/and or therapy for seizures associated with epilepsy or disorders where the controlled alteration of inhibitory drive may be beneficial. The present disclosure addresses these needs.

BRIEF SUMMARY OF THE DISCLOSURE

The present disclosure relates to compositions and methods for use in prophylaxis and/or therapy of seizures. Aspects of the disclosure relate in part to the surprising demonstration that recombinant adeno-associated virus (rAAV) can be used to restrict expression of a transgene in GABA-ergic interneurons in adult mammals using an I56i enhancer element that is provided in cis.

In general, the rAAV of this disclosure comprise a polynucleotide comprising i) an I56i enhancer sequence, and ii) a sequence encoding hM3Dq modified muscarinic receptor (Gq-DREADD) receptor. Thus, in certain embodiments the disclosure comprises methods for prophylaxis and/or therapy for seizures in an individual in need thereof.

Embodiments of the disclosure comprise administering to an individual a recombinant adeno-associated virus (rAAV) comprising: i) a I56i enhancer sequence, and ii) a sequence encoding hM3Dq modified muscarinic receptor (Gq-DREADD), such that the Gq-DREADD is expressed in interneurons of the individual. Thus, in one aspect the disclosure provides for converting interneurons in an individual that do not express Gq-DREADD to Gq-DREADD-expressing neurons. As such, the Gq-DREADD expression is linked to the presence of the I56i enhancer that is also provided as a component of the rAAV genome.

In an embodiment the disclosure comprises a method for prophylaxis and/or therapy for seizures comprising introducing into an individual an rAAV comprising: i) a I56i enhancer sequence, and ii) a sequence encoding Gq-DREADD, and subsequently administering to the individual an effective amount of an agonist of the Gq-DREADD such that the severity of the seizures are reduced or the seizures are prevented. In certain implementations the individual is experiencing a seizure at time of the administering the agonist of the Gq-DREADD receptor, and the severity of the seizure is reduced subsequent to the administering agonist. In embodiments the individual may be experiencing, or is at risk for developing, a partial seizure or a generalized seizure. In embodiments the individual has, is suspected of having, or has been diagnosed with epilepsy, including but not necessarily limited to pharmaco-resistant epilepsy.

Embodiments of the disclosure are illustrated using a representative Gq-DREADD agonist in the form of clozapine-N4-oxide (CNO), but any suitable agonist of the Gq-DREADD can be used.

An aspect of this disclosure comprises the surprising discovery of restricted expression of the Gq-DREADD only in GABA-ergic interneurons in the individual, and this includes but is not necessarily limited to such restricted expression adult mammals. The disclosure thus encompasses treating humans.

It will be apparent that the disclosure includes a method for prophylaxis and/or therapy for seizures in an individual in need thereof, wherein neurons of the brain of the individual already comprise the I56i enhancer sequence and a sequence encoding the Gq-DREADD, such as by having been previously administered an rAAV of this disclosure. The method comprises administering to such an individual an effective amount of an agonist of the Gq-DREADD receptor such that one or more seizures in the individual are inhibited or prevented.

In an embodiment the disclosure includes an expression vector or recombinant adeno-associated virus (rAAV) comprising i) a I56i enhancer sequence, and ii) a sequence encoding hM3Dq modified muscarinic receptor (Gq-DREADD), wherein the enhancer and the sequence encoding the G1-DREADD are present in the same rAAV genome (i.e., are provided in cis), and such compositions may be provided in any suitable pharmaceutical formulation(s).

Cells and cell cultures comprising the rAAV of this disclosure, isolated and/or purified rAAV preparations, and methods of making the rAAV of this disclosure are included. Kits for making and using the rAAV can also be provided.

BRIEF DESCRIPTION OF THE FIGURES

(FIGS. 1A, 1B, 1C, 1D, 1E and 1F): rAAV viruses containing the indicated enhancer/promoter and driving the green fluorescent reporter GFP were added to mice primary cortical culture at DIV8 (8 days in vitro) and were analyzed by immunostaining at DIV19 using the indicated antibodies. Arrows in A-F indicate GFP-expressing cells. Note the lack of GFP/Gad67 co-localization in panels A and F, demonstrating that only the mI56i confers specificity of expression within GABA-ergic interneurons. A scheme of the viral construction is shown for all virus tested. (FIG. 1G) Quantification of specificity of infection calculated as the percentage of GFP+ cells co-expressing Gad67. FIG. 1H. In Situ hybridization of Dlx5 gene mRNA at the indicated developmental stages (E13.5; P4; P21) from Allen Mouse Developing Brain Atlas (developingmouse.brain-map.org). Anatomical boundaries of neocortex (Cx) and striatum (Str) are indicated by dashed lines. The intense (dark) staining is only present at early embryonic stages and completely absent at later embryonic stages and postnatal stages. ITR: Internal terminal repeat; WPRE: woodchuck hepatitis post-transcriptional regulatory element; BGH: bovine growth hormone polyadenylation signal; SV40: polyomavirus simian virus 40 polyadenylation signal; phβg: human beta-globin minimal promoter; Angle: chimeric intron; I56i: enhancer mI56i from Dlx5/6 intergenic region; pLhx6: 1.6 kb promoter region in 5' of the coding sequence of Lhx6; pCamKII: promoter regions of Cam Kinase II. Data are represented as mean±s.e.m.

(FIG. 2A-J) Adult wild type or Dlx6a-Cre::Ai9 mice were stereotactically injected with 50-100 nl of rAAV-mI56i-GFP in somatosensory cortex (S1), hippocampus (CA1) and striatum, and were analyzed by immunostaining for the indicated markers after 7 days. (FIG. 1A) Representative example of GFP expression in the indicated brain regions. (FIG. 2B-G) and co-localization between GFP and the indicated marker in the indicated brain region. In B-D, arrows indicate cells with GFP-expression. Please note the high degree of co-localization between GFP and the indicated pan-interneuron marker. In E-G, arrows indicate cells co-localizing with the corresponding marker to specific interneuron subpopulations. (FIG. 2. H-J) Quantification of the proportion of cells co-expressing GFP and the indicated marker in the indicated anatomical regions. ITR: Internal terminal repeat; WPRE: woodchuck hepatitis post-transcriptional regulatory element; SV40: polyomavirus simian virus 40 polyadenylation signal; phβg: human beta-globin minimal promoter; Angle: chimeric intron; I56i: enhancer mI56i from Dlx5/6 intergenic region; Dashed lines represent limits of the indicated anatomical structures. Roman numbers represent cortical layers, O: oriens; P: pyramidal; R: radiatum; LM: laconosum moleculare. Data are represented as mean±s.e.m. Scale bars represent 15 μm (B-G) or 100 μm (A).

(FIG. 3A) Adult zebra finches (bird) were stereotactically injected with 50-100 nl of rAAV-mI56i-GFP in HVC, and were analyzed by immunostaining for the GFP and GABA after 2 weeks. (FIG. 3B) Juvenile Ferrets were stereotactically injected with 500 nl of rAAV-mI56i-GFP in V1, and were analyzed by immunostaining for GFP and Gad67 after 3 weeks. (C) Interneuron derived from human Embryonic Stem Cells (hESC) expressing Citrine under the control of Lhx6 were infected with rAAV-hI56i-Gq-DREADD-dTomato after 45 of in vitro culture (DIV45) and analyzed by immunostaining for the dTomato, Citrine, Human Cytoplasm after 2 weeks. Arrows indicate GFP- or RFP-expressing cells. Please note the high degree of co-localization between GFP- or RFP- and the indicated pan-interneuron marker. Quantification of the proportion of cells co-expressing GFP and the indicated marker is shown on the right panels. Anatomical boundaries are indicated by dashed lines. Data are represented as mean±s.e.m. Scale bars represent 25 μm (B,C) and 50 μm (A).

(FIG. 4A-I) Adult mice were stereotactically injected with 50-100 nl of rAAV-hI56i-Gq-DREADD in somatosensory cortex (S1) and were either analyzed by immunostaining for the indicated markers after 7 days (A) or 300 μm vibratome sections were generated for electrophysiological recording (FIG. 4B-I). (FIG. 4A) Representative example of colocalization between dTomato and HA-tagged Gq-DREADD in somatosensory cortex layer VI. Note the expected membrane localization of the Gq-DREADD. (FIG. 4B). Population data of effect of CNO on membrane potential. Average membrane potential for 25 sec 30 min pre- and 2 min post-CNO. (FIG. 4C) Average change in membrane potential for FS and LTS cells. (FIG. 4D) Representative example of biocytin dTomato positive cells showing typical neocortical interneuron morphology. (FIG. 4E) Representative membrane potential of cells in response to a negative (dark gray), rheobase (black) and twice rheobase (light gray) current pulse. Baseline membrane potential is −60 mV. Note the typical fast-spiking and low-threshold spiking profile (top and bottom panel respectively). (FIG. 4F) Effect of CNO on membrane potential. Horizontal dash line indicates baseline membrane potential (~60 mV). (FIG. 4 G,I) Effect of CNO on inhibitory drive. (FIG. 4G) Change of inhibitory drive calculated as the difference of inhibitory charge per second over a period of 25 sec between 30 min before and 5 min after bath application of CNO for a cell patched outside or inside the injection site. (FIG. 4H) Voltage clamp traces of a cell patched outside and inside the injection site. Vertical dash line indicates CNO entry in the bath. Insets below traces show expanded version of 5 sec before and after CNO. (FIG. 4I). Post-hoc immunostaining of a biocytin-filled pyramidal neuron (cell indicated with arrowhead in the upper panel) surrounded by interneurons infected by the rAAV-hI56i-HA-Gq-DREADD-P2A-NLS-dTomato (round nuclear-staining in the lower panel) within the site of viral injection. White arrowheads points at the recorded cell. Data are represented as mean±s.e.m (FIG. 4B,C,F). Unpaired T-test: ***=p-value<0.001, n.s.=non-significant. Scale bars represent 10 μm. Vertical dash lines indicate CNO entry in the bath.

DESCRIPTION OF THE DISCLOSURE

Figure 1:
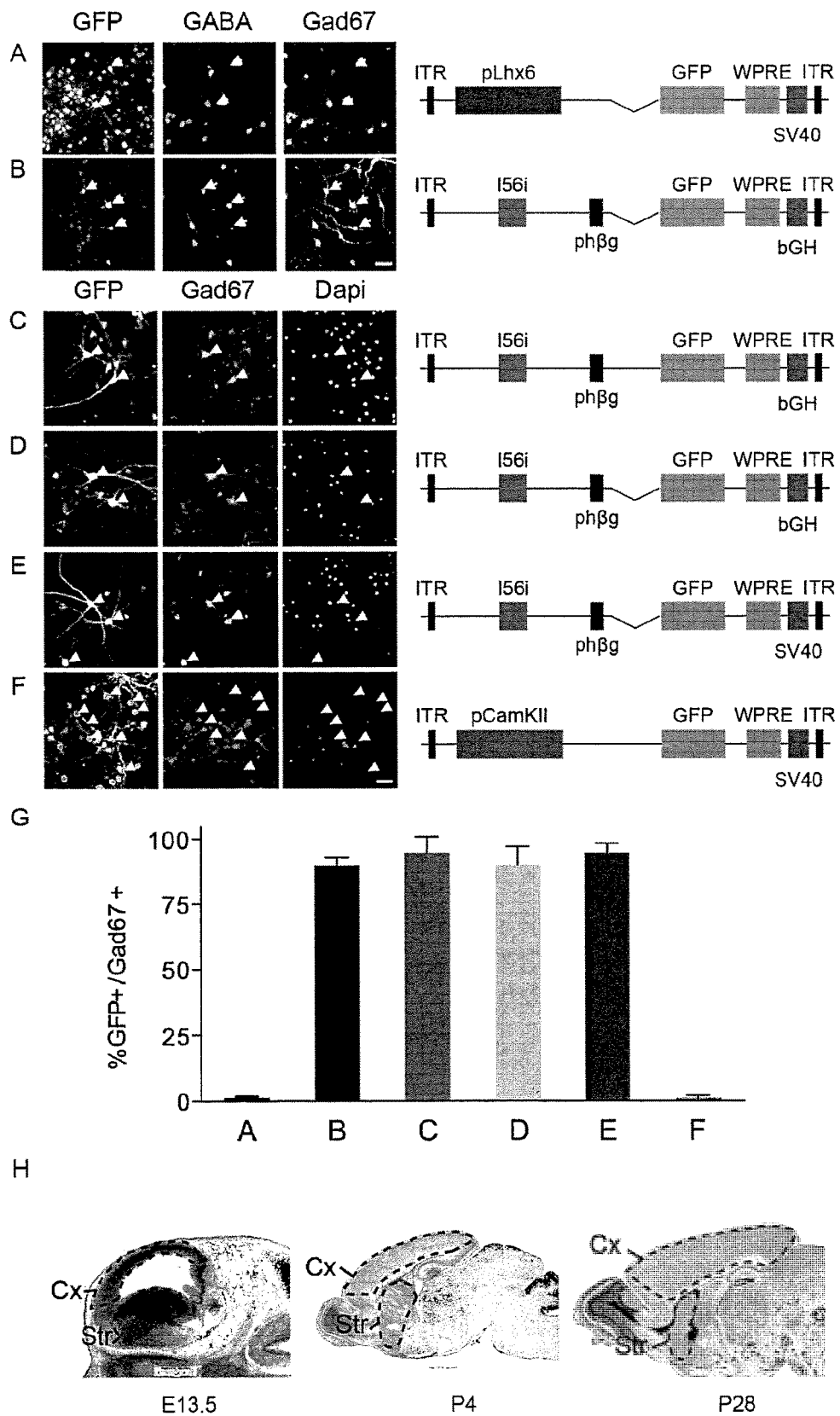
FIG. 1. rAAV-mI56i-GFP shows high specificity for GABAergic interneurons in vitro.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all polynucleotide and amino acid sequences described herein, and every polynucleotide sequence referred to herein includes its complementary DNA sequence, and also includes the RNA equivalents thereof to the extent an RNA sequence is not given. Every DNA and RNA sequence encoding polypeptides disclosed herein is encompassed by this disclosure, including but not limited to sequences encoding all recombinant proteins that comprise a segment of or a full protein, as described further below.

The present disclosure comprises compositions and method for prophylaxis and/or therapy for seizures associated with epilepsy, or neurological dysfunction that would be ameliorated by increase of inhibitory tone.

The present disclosure relates to an innovative pharmacogenetic approach to achieve localized suppression of neuronal excitability at seizure foci while preserving the intrinsic architecture and functionality of brain circuitry.

The compositions include, but are not necessarily limited to, recombinant adeno-associated virus (rAAV) comprising: i) an I56i enhancer sequence, and ii) a sequence encoding hM3Dq modified muscarinic receptor (Gq-DREADD) receptor. The I56i enhancer is operably linked to the sequence encoding the Gq-DREADD receptor. By "operably linked" it is meant that the enhancer sequence is present in the same rAAV genome as the sequence encoding the Gq-DREADD receptor (and is thus provided in cis), and expression of the Gq-DREADD receptor is dependent on the presence of the enhancer in the rAAV genome. Thus, and without intending to be constrained by any particular theory, because it is believed (and demonstrated herein) that interneurons are the only cell type that express transcription factors that can bind to the I56i enhancer, expression of the Gq-DREADD is restricted to the interneurons into which the rAAV is introduced. In this regard, those skilled in the art will readily recognize how to distinguish an interneuron from other cell types, including other types of neurons, using well known parameters. In non-limiting examples GABAergic interneurons can be distinguished from other cell types by the expression of the genes Gad65 and Gad67; in the adult cortex, GABAergic interneurons can be distinguished from glutamatergic excitatory neurons by the presence of GABA. In the adult striatum, GABAergic interneurons can be distinguished from Medium Spiny Neurons by the expression of the gene Nkx2.1. (See, for example, Rudy, B., Fishell, G., Lee, S. & Hjerling-Leffler, J. Three groups of interneurons account for nearly 100% of neocortical GABAergic neurons. *Devel Neurobio* 71, 45-61 (2011)): Kepecs, A. & Fishell, G. Interneuron cell types are fit to function. *Nature.* 505, 318-326 (2014).

Methods of this disclosure comprise introducing the modified rAAVs into neuronal cells in the brain of an individual in need thereof, and subsequently administering to the individual a Gg-DREADD agonist such that seizures in the individual are reduced. Reducing the seizures comprises reducing the frequency and/or intensity of the seizures, which may also accordingly comprise preventing the onset of a seizure, or abolishing a seizure in progress.

As is known in the art, "DREADD" stand for "Designer Receptors Exclusively Activated by Designer Drugs." The disclosure accordingly encompasses activating the Gq-DREADD receptor using any suitable Gq-DREADD agonist, examples of which are known in the art (see, for example, Chen, X. et al. *The First Structure—Activity Relationship Studies for Designer Receptors Exclusively Activated by Designer Drugs.* ACS Chem. Neurosci. 6, 476-484 (2015), the disclosure of which is incorporated herein by reference).

In certain and non-limiting embodiments, the Gq-DREADD agonist comprises clozapine-N4-oxide (CNO). In an embodiment the agonist is Perlapine (also referred to as 6-(4-methyl-1-piperazinyl)morphanthridine, and 6-(4-methylpiperazin-1-yl)-11H-benzo[c][1]benzazepine). In another embodiment the Gq-DREADD agonist comprises a compound known in the art as "Compound 21". Compound 21 has a chemical formula derived from CNO and is described in Chen, X. et al. *The First Structure— Activity Relationship Studies for Designer Receptors Exclusively Activated by Designer Drugs. ACS Chem. Neurosci.* 6, 476-484 (2015). The disclosure includes using combinations of distinct Gq-DREADD agonists.

In connection with the present disclosure, and as is well known in the art, enhancers and promoters are found in non-coding genomic DNA and regulate the expression of genes through a wide variety of mechanisms; regulation of gene expression dictates, among other factors, whether or not the gene is expressed, at what point in time it is expressed, and in which specific cellular types and subtypes the particular gene is expressed. Enhancers and promoters have been extensively shown to restrict expression of a variety of genes to specific periods of time and specific cell-types in transgenic mice. For example, the enhancer known in the art as the Dlx5/6 enhancer has been demonstrated to be responsible for the endogenous control of expression of Dlx5 and Dlx6 genes in mice. The Dlx5/6 enhancer, which reside in the Dlx5/6 intergenic region, is also known as the I56i enhancer. In transgenic mice, this enhancer has been demonstrated to restrict the expression of a reporter protein exclusively to cells endogenously expressing Dlx5 and Dlx6 (Zerucha, T. et al. A highly conserved enhancer in the Dlx5/Dlx6 intergenic region is the site of cross-regulatory interactions between Dlx genes in the embryonic forebrain. Journal of Neuroscience 20, 709-721 (2000); Starner, T., Puelles, L., Ekker, M. & Rubenstein, J. L. R. Expression from a Dlx gene enhancer marks adult mouse cortical GABAergic neurons. Cerebral Cortex 12, 75-85 (2002); Monory, K. et al. The endocannabinoid system controls key epileptogenic circuits in the hippocampus. 51, 455-466 (2006); Miyoshi, G. et al. Genetic Fate Mapping Reveals That the Caudal Ganglionic Eminence Produces a Large and Diverse Population of Superficial Cortical Interneurons. Journal of Neuroscience 30, 1582-1594 (2010)). Similarly, a promoter known in the art as the Lhx6 promoter has been demonstrated to be responsible for the endogenous expression of the Lhx6 gene in mice, and in transgenic mice, the Lhx6 promoter was shown to restrict the expression of a reporter exclusively to cells endogenously expressing Lhx6. Gong, S. et al. A gene expression atlas of the central nervous system based on bacterial artificial chromosomes. 425, 917-925 (2003)). However, transgenic mice do not provide a reliable basis for predicting how a promoter or an enhancer element will function when such elements are introduced into neurons using a recombinant virus, such as an rAAV as the delivery vehicle.

In more detail, in the cortex, Dlx5, Dlx6 and Lhx6 genes are expressed at high level in GABAergic interneurons, but only during embryonic development. Expression of these genes is absent in this region in mice and humans after birth. In addition, in the striatum, Dlx5 and Dlx6 genes are expressed at high level in GABAergic interneurons and in Medium Spiny Neurons during embryonic development in mice but are absent in this region adult mice.

In view of these known patterns of gene expression in wild type and transgenic mice that are modulated by the I56i enhancer and the Lhx6 promoter, the present disclosure provides unexpected results that, without intending to be constrained by any particular concept, are illustrated by at least the following three points.

Figure 4:
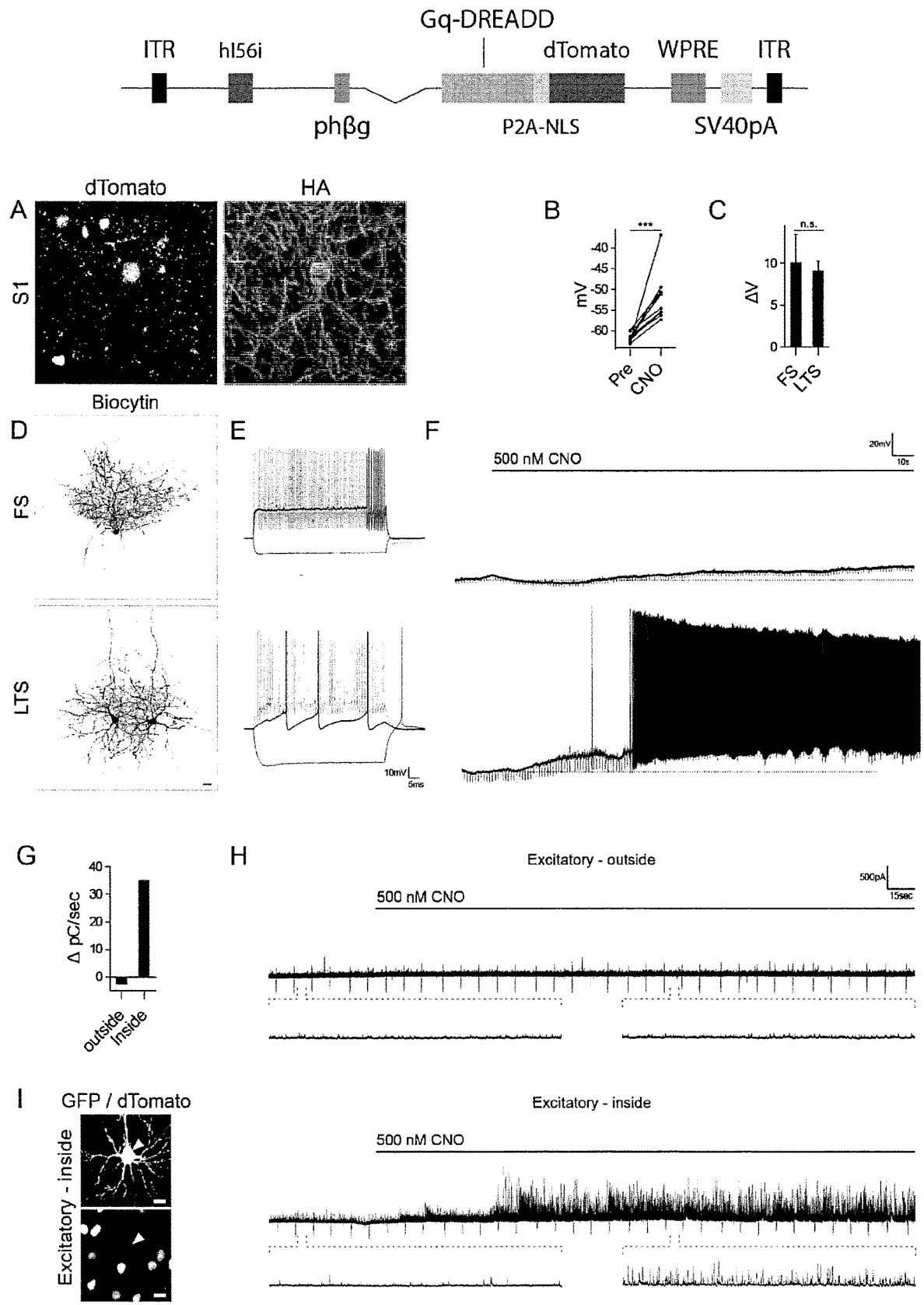
FIG. 4. rAAV-hI56i-Gq-DREADD shows a CNO-dependent alteration of local neuronal activity.

First, as described above, in transgenic mice both the I56i enhancer and the Lhx6 promoter have been previously shown to recapitulate the expression profile of the gene they control endogenously. However, in the present disclosure, it is demonstrated that when provided as a component of a rAAV genome, the I56i enhancer, but not the Lhx6 promoter, restricts gene expression to GABA-ergic interneurons, in contrast to the transgenic mouse models. (See, for example, FIG. 1 demonstrating that the I56i enhancer, but not Lhx6-promoter, restricts the expression of the reporter green fluorescent protein (GFP) to GABA-ergic interneurons). In this regard, it should be noted that rAAV infects all cell-types without selectivity. Further, all cell types have within their chromosomes an endogenous I56i enhancer and Lhx6 promoter sequences. Accordingly, the disclosure includes the demonstration that providing I56i in cis via the rAAV construct correlates with expression of Gq-DREADD to which the enhancer is linked in cis, and that this expression is only in GABA-ergic interneurons (see, for example, FIG. 4). This could not be predicted from transgenic animal models because the Lhx6 promoter—also provided in a cis linkage with a reporter gene in an rAAV—does not drive expression of the reporter at all in GABA-ergic interneurons, as shown in FIG. 1.

Second, the endogenous Dlx5 and Dlx6 genes are not expressed after birth in either mice and humans. As such, the I56i enhancer does not endogenously function in any cells after birth to facilitate expression of the Dlx5 and Dlx6 genes. Accordingly, if the I56i enhancer in rAAV recapitulated its endogenous function to promote expression of genes with which it is linked in cis (i.e., Dlx5 and Dlx6), it would not be expected for an rAAV containing the enhancer to drive any gene expression in any cells after birth. As such, the expression would be expected to be restricted to embryonic stages, which are not therapeutically relevant. In contrast, the present disclosure demonstrates that an rAAV approach to provide the enhancer in a cis linkage to a transgene (be it a reporter or a Gq-DREADD) results not only in expression of the gene in neuronal cells after birth, but moreover is restricted to GABA-ergic interneurons, and this is shown in adult mice. Specifically, FIG. 4 demonstrates that expression of Gq-DREADD using rAAVs of the present disclosure is restricted to GABA-ergic interneurons in adult mice. This is in contrast to what is shown in FIG. 1H, namely, in situ hybridization of the Dlx5 gene mRNA in mouse at different developmental stages. FIG. 1H shows that the Dlx5 gene is highly expressed in the cortex and striatum of the embryonic brain at embryonic developmental day 13.5 (E13.5) but absent postnatally, as illustrated in P4 and P28 (4 and 28 days after birth) brain. These data therefore demonstrate that the enhancer does not recapitulate the endogenous expression of the Dlx5 and Dlx6 genes, and the knowledge of the expression profile of the endogenous Dlx5 and Dlx6 genes is not only not predictive of the ability of the enhancer to drive or restrict expression to a particular stage or cell type, it leads to an expectation that expression in non-embryonic cells would not occur. The presently provided results are accordingly unexpected.

Third, before birth in the striatum, the Dlx5 and Dlx6 genes are expressed in both GABA-ergic interneurons and GABA-ergic Medium Spiny Neurons. Specifically, in the striatum both GABA-ergic interneurons and the GABA-ergic (projection) medium spiny neurons (4% and 96% of the population respectively) express high levels of Dlx5 or Dlx6 during embryonic development. If the Dlx5/6 (I56i) enhancer in rAAV accurately recapitulated the endogenous expression profile of Dlx5 and Dlx6 genes, it would be expected that the rAAV comprising the enhancer would drive expression in both GABA-ergic interneurons and GABA-ergic Medium Spiny Neurons. But in contrast, the present disclosure demonstrates that the rAAV comprising the enhancer restricts the expression to GABA-ergic interneurons but not in GABA-ergic Medium Spiny Neurons (see, for example, FIG. 4D). Therefore, the instant disclosure demonstrates that the enhancer, when provided in the context of an rAAV, does not recapitulate the endogenous expression of the Dlx5 and Dlx6 gene. Moreover, the expression of reporter proteins and a functional Gq-DREADD that is restricted to adult GABA-ergic interneurons, and the lack of expression in medium spiny neurons, is a surprising result.

Non-limiting embodiments of this disclosure are demonstrated in adult mice, ferret, gerbil, human Embryonic Stem Cell (hESC)-derived interneurons, and electrophysiology on mouse brain slice. However, and as will be recognized by those skilled in the art, because the present disclosure includes a method for modifying interneurons so that they comprise the I56i enhancer and the Gq-DREADD receptor wherein the excitability of interneurons increase as a result of the Gq-DREADD binding its ligand, and that this can result in CNO-dependent increase of interneuron activity in every region of the brain, it is feasible for the present disclosure to have additional therapeutic applications that extend beyond epilepsy, including but not necessarily limited to neuropsychiatric disorders, Parkinson's, addiction of various etiologies, movement disorders such as those benefiting from deep brain stimulation, obesity, etc.

Given the benefit of this disclosure, the rAAV can be made by the skilled artisan using standard techniques and commercially available reagents. In this regard, gene therapy using non-pathogenic rAAV is showing increasing promise for both mono-allelic diseases and complex diseases. There is an increasing number of phase I-III clinical trials using AAV vectors that have yielded promising results, and in 2012, the first AAV based therapy received marketing approval by the European Union (Kotterman, M. A. & Schaffer, D. V. Engineering adeno-associated viruses for clinical gene therapy. Nat. Rev. Genet. 15, 445-451 (2014).

Suitable vectors that can be adapted to comprise the I56i enhancer and encode the Gq-DREADD receptor given the benefit of the present disclosure are commercially available from, for example, the CLONTECH division of TAKARA BIO. In certain implementations plasmid vectors may encode all or some of the well-known rep, cap and adeno-helper components. The rep component comprises four overlapping genes encoding Rep proteins required for the AAV life cycle (Rep78, Rep68, Rep52 and Rep40). The cap component comprises overlapping nucleotide sequences of capsid proteins VP1, VP2 and VP3, which interact together to form a capsid of an icosahedral symmetry. Another plasmid providing the Adeno Helper function may also be co-transfected. The helper components comprise the adeno-viral genes E2A, E4orf6, and VA RNAs for viral replication.

The amino acid sequence of the Gq-DREADD receptor is well known in the art, and the instant disclosure includes all polynucleotide sequences encoding the Gq-DREADD receptor. In embodiments, the polynucleotides encoding the Gq-DREADD in the rAAV can be modified, for example, by including optimized codons for expression of the Gq-DREADD receptor in human interneurons.

The amino acid sequence of the Gq-DREADD (hM3Dq) receptor is known (Armbruster et al., PNAS, Evolving the lock to fit the key to create a family of G protein-coupled receptors potently activated by an inert ligand, 104, 5163-5168 (2007)). It is a derivative of the amino-acid sequence of the human muscarinic acetylcholine receptor M3 in which the tyrosine in position 149 is replaced by a cysteine and the arginine in position 239 is replaced by a glycine. The unmodified human sequence is given in NCBI accession no. NP 000731.1. The modified sequence (SEQ ID NO: 1)
mtlhnnsttsplfpnissswihspsdaglppgtvthfgsynvsraag nfsspdgttddplgghtvwqvvfiaftgilalvtiignilvivsfkv nkqlktvnnyfllslacadliigvismnlfttyiimnrwalgnlacd lwlaid@vasnasvmnllvisfdryfsitrpltyrakrttkragvmi glawvisfvlwapailfwqyfvgkrtvppgecfiqflseptitfgta ia@fympvtimtilywriyketekrtkelaglqasgteaetenfvhp tgssrscssyelqqqsmkrsnrrkygrchfwftttkswkpsseqmdqd hsssdswnnndaaaslensassdeedigsetraiysivlklpghsti lnstklpssdnlqvpeeelgmvdlerkadklqaqksvddggsfpksf sklpiqlesavdtaktsdvnssvgkstatlplsfkeatlakrfalkt rsqitkrmrmslvkekkaaqtlsaillafiitwtpynimvlvntfcd scipktfwnlgywlcyinstvnpvcalcnktfrttfkmlllcqcdkk krrkqqyqqrqsvifhkrapeqal.

The I56i enhancer is also well characterized. The present disclosure includes use of any I56i enhancer sequence from any species, provided the enhancer will function to promote expression of the Gq-DREADD receptor in interneurons. In embodiments, the I56i enhancer comprises or consists of 297 nucleotides (nt). In embodiments, the I56i enhancer sequence comprises a contiguous DNA sequence that is from 85%-100% identical across the length of the 297 nt I56i enhancer sequence from *Homo sapiens*. The *Homo sapiens* I56i nt sequence is: CAGGATCAATTCT-GAACAAAGCCTCCAGCTGCAGTGCCATCCAATTT-GAAGCAGACAT TGGGGACAATTTAAGGTTTTTATC-CACAAGAAGGTTTTTTTCCATTCTCTTAAATGCAGC CATAATTAGAGTAATTTTTCATGTAGCCCGCTGAT-TACAGCGTTTTTACCGTCAAAGAT AATTACCTGTA-ATTTTCTTCCACTTTTAATACTAAAAAGCCATCTTT-ATTTAGATTCAGG AACAGGAAAGGCGAAACAAA-AGAGGGAAATTATTCTGTTATTCATACACAAATT-GCAG AG (SEQ ID NO:2). In embodiments the mouse I56i enhancer sequence is used, or a sequence that is 80-99% identical to it is used. The mouse sequence is also known and is available under GenBank No. AC_000028.1, the sequence of which is incorporated herein by reference as provided in GenBank as of the date of filing of this application or patent. In embodiments the zebrafish I56i enhancer sequence is used, or a sequence that 80-99% identical to the human sequence is used. The zebrafish sequence is also known and is available under GenBank No. NC_007130.6, the sequence of which is incorporated herein by reference as provided in GenBank as of the date of filing of this application or patent.

It will be recognized by those skilled in the art that, because it is an enhancer, the orientation of the enhancer sequence, i.e., 5'-3', or 3'-5', is not material to its function. As such, the present disclosure includes the enhancer sequences as presented herein, their reverse orientation, and their reverse-complementary sequences. Additionally, there is no requirement for specific spacing of the enhancer relative to other sequence, such as the Gq-DREADD coding sequence, so long as the enhancer and the coding sequence are provided in the same rAAV genome.

Polynucleotides encoding rAAVs of this disclosure can comprise additional elements that will be apparent to those skilled in the art, given the benefit of the present disclosure. In certain examples, the polynucleotides comprise sequence encoding a detectable marker, such as fluorescent protein, and may comprise an element such as a Woodchuck hepatitis virus Posttrascriptional Regulatory Element (WPRE), which is believed to increase RNA stability and protein yield. The polynucleotide may also comprise a promoter to drive transcription of one or more genes inserted between inverted terminal repeats (ITRs). The polynucleotides may also comprise a polyadenylation signal such as bovine growth hormone polyadenylation signal and/or SV40 polyomavirus simian virus 40 polyadenylation signal. The polynucleotide can comprise a minimal promoter, such as a human beta-globin minimal promoter (phβg) and a chimeric intron sequence (i.e., Hermeming et al., 2004 Journal of Virological Methods [2004, 122(1):73-77]). Without intending to be constrained by any particular theory it is considered that ITRs aid in concatamer formation in the nucleus after the single-stranded vector DNA is converted by host cell DNA polymerase complexes into double-stranded DNA. It is accordingly believed that administration of the rAAVs of this disclosure will form episomal concatemers in the nucleus of cells into which they are introduced. In non-dividing cells, such as adult interneurons, it is believed these concatemers remain intact for the life of the interneurons. It is also expected that integration of rAAV polynucleotides into host chromosomes will be negligible or absent and will not affect expression of regulation of any human gene.

In various embodiments, the disclosure includes isolated and/or recombinant polynucleotides comprising the enhancer and encoding the Gq-DREADD receptor, expression vectors comprising such polynucleotides, cells comprising the polynucleotides, cells comprising rAAV encoded by the polynucleotides, isolated preparations of such rAAV particles, and pharmaceutical preparations comprising the rAAV particles.

In various aspects of the invention, methods of making the rAAVs are provided. In general, the method of making the rAAvs comprises culturing cells which comprise an expression vector encoding an rAAV of this disclosure, allowing expression of the polynucleotides to produce the rAAVs, and separating the rAAVs from cells in the cell culture and/or from the cell culture media. The rAAVs can be purified to any desired degree of purity using conventional approaches.

rAAvs of the invention can be mixed with any pharmaceutically acceptable buffer, excipient, carrier and the like to form a pharmaceutical preparation. Suitable pharmaceutical compositions can be prepared by mixing rAAVs with a pharmaceutically-acceptable carrier, diluent or excipient, and suitable such components are well known in the art. Some examples of such carriers, diluents and excipients can be found in: Remington: The Science and Practice of Pharmacy (2005) 21st Edition, Philadelphia, Pa. Lippincott Williams & Wilkins.

In general, a composition comprising a rAAV can be administered to any individual in need thereof. In certain embodiments of disclosure facilitates conversion of interneurons in an individual that do not express Gq-DREADD into Gq-DREADD-expressing interneurons by administering to the individual an rAAV that comprises the I56i enhancer sequence and the sequence encoding the Gq-DREADD, such that the Gq-DREADD is expressed in interneurons of the individual. The disclosure provides a demonstration of this, and moreover shows that the Gq-DREADD expressed in the interneurons is responsive to a Gq-DREADD agonist (see, FIG. 4, G-I).

In embodiments, the subject is undergoing, has experienced, and/or is at risk for a neurological disorder that would ameliorated by the controlled increase in inhibitory tone, including but not limited to individuals experiencing a seizure, and thus may be diagnosed with, or is suspected of having a seizure disorder. In embodiments the individual in need is a human or a non-human animal, the latter being applicable for veterinary purposes. The rAAV can be administered using any suitable approach, such as intracranial injection or intravenous injections.

As will be recognized in the art, a characteristic that distinguishes categories of seizures is whether the seizure activity is partial (e.g., focal) or generalized. In an embodiment, the compositions and methods of the present disclosure are used to treat partial and/or generalized seizures. In an embodiment the disclosure relates to treatment of pharmaco-resistant epilepsy and/or a replacement of a pharmacological treatment.

In more detail, epilepsy and related disorders and their attendant seizure symptoms are well characterized in the art. In this regard, the present disclosure is expected to be pertinent to any subject, such as an adult human, child, or infant, who experiences or is at risk for experiencing one or more seizures. In certain embodiments a composition comprising rAAVs of this disclosure is administered to an individual whose interneurons do not, at the time of administration, express any gene that is dependent on the I56i enhancer for expression. In embodiments, a composition comprising rAAVs of this disclosure is administered to an individual whose interneurons no longer express the Dlx5 and Dlx6 genes. In embodiments, a composition comprising rAAVs of this disclosure is administered to an individual who is at least one month old. In embodiments, the individual is at least 1, 2, 3, 4, 5, 6, 7, 8, 9, 10, 11, 12, 13, 14, 15, 16, 17 or 18 years of age.

In embodiments, the disclosure relates to treating one or more seizure disorders which include but are not limited to, epilepsy (including, but not limited to, localization-related epilepsies, generalized epilepsies, epilepsies with both generalized and/or local seizures, and the like), seizures associated with Lennox-Gastaut syndrome, seizures as a complication of a disease or condition (such as seizures associated with encephalopathy, phenylketonuria, juvenile Gaucher's disease, Unvericht-Lundborg's progressive myoclonic epilepsy, stroke, head trauma, stress, hormonal changes, drug use or withdrawal, alcohol use or withdrawal, sleep deprivation, fever, infection, brain cancer, and the like), or chemically-induced seizure disorders.

In general a composition comprising rAAVs of this disclosure can be administered to any individual in need thereof. In embodiments, the subject to whom a composition of this disclosure is administered is undergoing, has experienced, and/or is at risk for experiencing a seizure, and thus may be diagnosed with or be suspected of having any seizure disorder. In embodiments the individual has been administered a rAAV of this disclosure at a time previous to the onset of the seizure and/or administering the Gq-DREAD agonist, and such time may be weeks, months or years before the administration. In this regard, it has been demonstrated that rAAV driven expression can last for at least 6 years in a non-human primate model (Rivera, V. M. et al. Long-term pharmacologically regulated expression of erythropoietin in primates following AAV-mediated gene transfer. Blood 105, 1424-1430 (2005)).

Epilepsy and related disorders and their attendant seizure symptoms are well characterized in the art. As will be recognized, a characteristic that distinguishes categories of seizures is whether the seizure activity is partial (e.g., focal) or generalized. In an embodiment, a composition of the present disclosure is used to treat partial and/or generalized seizures.

Partial seizures are considered those in which the seizure activity is restricted to discrete areas of the cerebral cortex. As is known in the art, if consciousness is fully preserved during the seizure, the seizure is considered to be a simple-partial seizure. If consciousness is impaired, the seizure is considered to be a complex-partial seizure. Within these types of seizures are included those that initiate as partial seizures and subsequently extend through the cortex; these are considered partial seizures with secondary generalization.

Generalized seizures encompass distant regions of the brain simultaneously in a bilaterally symmetric manner and can include sudden, brief lapses of consciousness, such as in the case of absence or petit mal seizures, without loss of postural control. Atypical absence seizures usually include a longer period of lapse of consciousness, and more gradual onset and termination. Generalized tonic-clonic or grand mal seizures, which are considered to be the main type of generalized seizures, are characterized by abrupt onset, without warning. The initial phase of the seizure is usually tonic contraction of muscles, impaired respiration, a marked enhancement of sympathetic tone leading to increased heart rate, blood pressure, and pupillary size. After 10-20 seconds, the tonic phase of the seizure typically evolves into the clonic phase, produced by the superimposition of periods of muscle relaxation on the tonic muscle contraction. The periods of relaxation progressively increase until the end of the ictal phase, which usually lasts no more than one minute. The postictal phase is characterized by unresponsiveness, muscular flaccidity, and excessive salivation that can cause stridorous breathing and partial airway obstruction. Atonic seizures are characterized by sudden loss of postural muscle tone lasting 1-2 seconds. Consciousness is briefly impaired, but there is usually no postictal confusion. Myoclonic seizures are characterized by a sudden and brief muscle contraction that may involve one part of the body or the entire body. It is considered that the present disclosure is applicable for prophylaxis and/or therapy of any of the foregoing types of seizures, which are described for illustration but are not meant to be limiting. In embodiments, the disclosure is pertinent to treatment of epilepsy. In embodiments, the epilepsy is selected from idiopathic, cryptogenic, symptomatic, general and focal epilepsy. In embodiments, the disclosure is pertinent to treatment of pharmacoresistant epilepsy. As used herein, the term pharmacoresistant epilepsy means an epilepsy that is not controlled despite use of at least two drugs that are suitable for the type of epilepsy and have been appropriately prescribed at maximum tolerated doses. In embodiments the pharmacoresistant epilepsy is one where three such drugs trials have failed to eliminate the seizures. Those skilled in the art will recognize that the chances of controlling epilepsy decline sharply after failure of the second or third antiepileptic drug trial, and thus the present disclosure provides an approach designed to address these failed treatment cases.

In embodiments, the disclosure includes administering a therapeutically effective amount of an rAAV to an individual. "Therapeutically effective amount" as used herein means that amount of rAVV that is introduced into a sufficient number of interneurons such that a seizure can be inhibited or prevented subsequent to the administration of the Gq-DREADD agonist to the individual. The amount of rAAV that is administered can be determined by those skilled in the art, given the benefit of the present disclosure and based on factors such as the size of the epileptic focus and the titer of the viral preparation, and from data acquired in non-human primates (e.g., Colle, M.-A. et al. Hum. Mol. Genet. 19, 147-158 (2010)). In certain embodiments from 10E+10 to 10E+12 rAAV particles are used to transduce the expression of Gq-DREADD to a therapeutically relevant number of interneurons.

The dosing of the Gq-DREADD agonist can be determined based on well-known parameters, and can be adjusted given the benefit of the present disclosure to provide, for example, sufficient Gq-mediated signaling such that adequate firing of the interneurons to inhibit or prevent a seizure is achieved. In general, a therapeutically effective amount of Gq-DREADD agonist is administered to an individual to whom an rAVV of this disclosure has been previously administered. A Gq-DREADD agonist can be administered via any suitable approach, such as systemically by intravenous injection, or by, for example, an osmotic minipump. In general it is expected that CNO or any other Gq-DREADD agonist could be administered acutely, such as a single dose in the range of 0.25 to 5 mg/kg, inclusive, to reduce the severity of a seizure that is in progress. Alternatively, the ligand could be administered chronically, such as in a dose in the range of 0.25 to 5 mg/kg every 6 to 12 hours. In certain approaches, a single administration injection is expected to reduce the severity of a seizure in progress. For seizure prophylaxis, long-term chronic treatment with the indicated dosing periods are expected to be adequate to prevent the onset and/or frequency of seizures, or reduce the severity of a seizure that occurs subsequent to the administration of the Gq-DREADD agonist.

The approaches of the present disclosure can also be combined with other anti-seizure modalities, including but not necessarily limited to use with other anti-epileptic therapeutic agents, and/or surgical techniques.

The following Examples are intended to illustrate but not limit aspects of this disclosure.

Example 1

This Example demonstrates interneuron specificity in vitro. Primary cortical neuronal culture from mice were infected with different rAAV constructs containing mI56i and various combinations of elements previously shown to influence the level of expression of genes delivered by rAAVs (FIG. 1A-F). The majority of cells expressing GFP also expressed the pan-interneuron marker GABA or GAD67 (~95%) when infected with all rAAVs containing the mI56i enhancer. The rAAV construct in FIG. 1E showed both the highest level of expression and specificity for GABAergic cells. This construct was therefore selected for additional experiments as described below. rAAVs containing the promoter region of the interneuron-specific gene Lhx6 or a promoter used to target excitatory neurons (non-interneuron) did not effectively restrict expression to GABAergic interneurons (FIG. 1G). Taken together, these data demonstrate the mI56i enhancer alone is sufficient to restrict the expression of a reporter to interneurons and demonstrate that targeting interneurons using rAAV is not trivial.

Example 2

Figure 2:
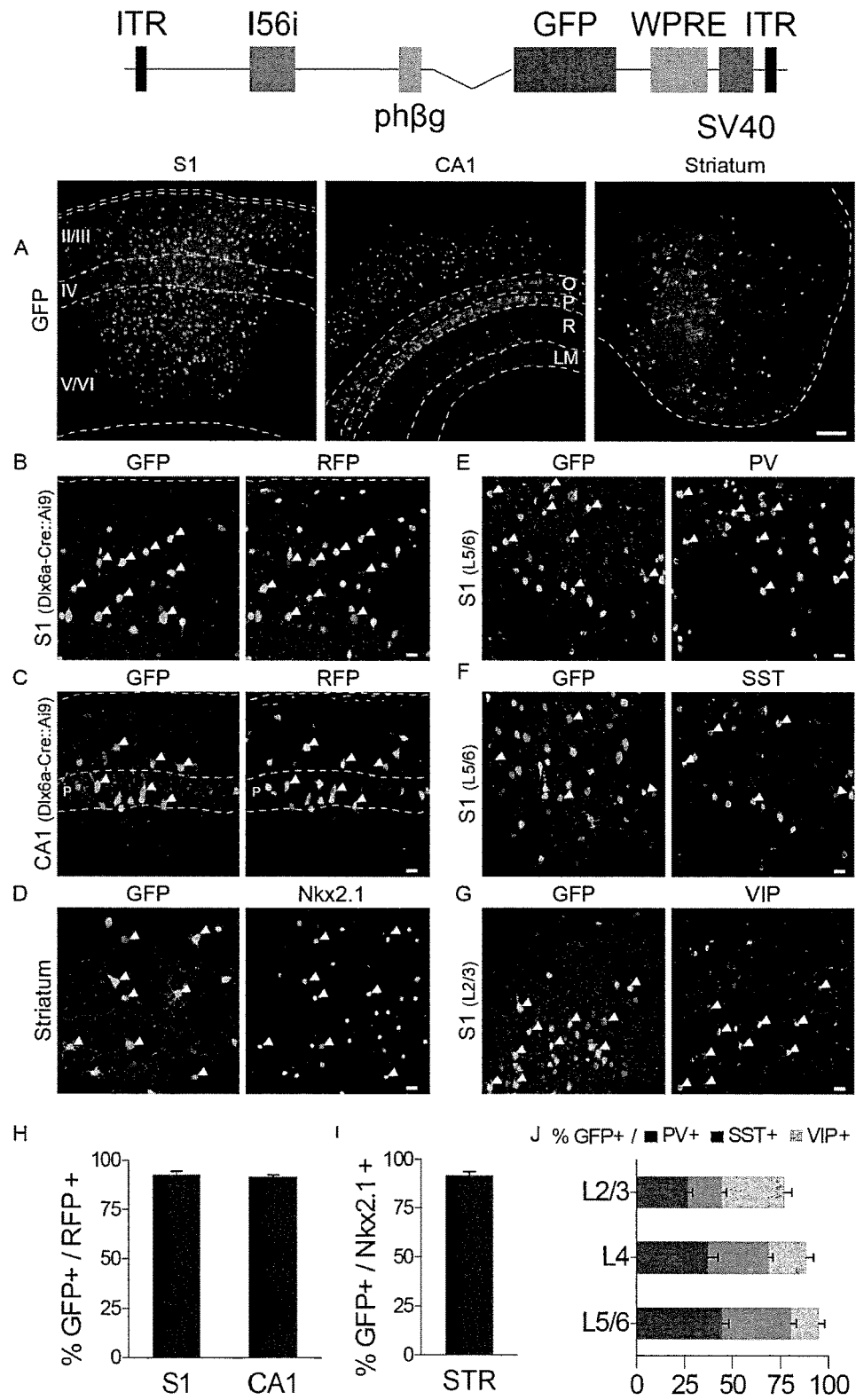
FIG. 2. rAAV-mI56i-GFP shows high specificity for GABAergic interneurons in vivo.

This Example demonstrates expression of rAAV-mI56i-GFP in interneurons in vivo. Immunofluorescence analyses of adult mice injected with the rAAV-mI56i-GFP revealed a sparse but intense GFP labeling in somatosensory cortex (S1), hippocampus and striatum one week after injection (FIG. 2A). The majority of infected cells co-expressed GABA in the cortex and hippocampus (data not shown) and the pan-interneuron marker Nkx2.1 in striatum (FIG. 2D,I). To confirm these findings, rAAV-mI56i-GFP was injected into the cortex and hippocampus of Dlx6aCre:Ai9 mice, where RFP expression is restricted to interneurons in these regions. Again, the majority of infected cells were co-labeled with RFP (FIG. 2B,C,H). These data show that the rAAV-mI56i-GFP drives expression of GFP specifically in interneurons in all the telencephalic regions tested in adult mice. In S1, the infected cells express parvalbumin (PV), somatostatin (SST) and vasoactive intestinal peptide (VIP) in proportions that correspond to the expected distribution of these 3 non-overlapping interneuron markers (FIG. 2E-G,J), indicating that the rAAV-mI56i-GFP is not restricted to specific interneuron subtypes. These results demonstrate for the first time that an rAAV containing the mI56i enhancer sequence exclusively results in selective expression within interneurons (but not GABAergic principal cells, such as those that include but are not limited to those that exist in the striatum, globus pallidus or medial amygdala).

Example 3

Figure 3:
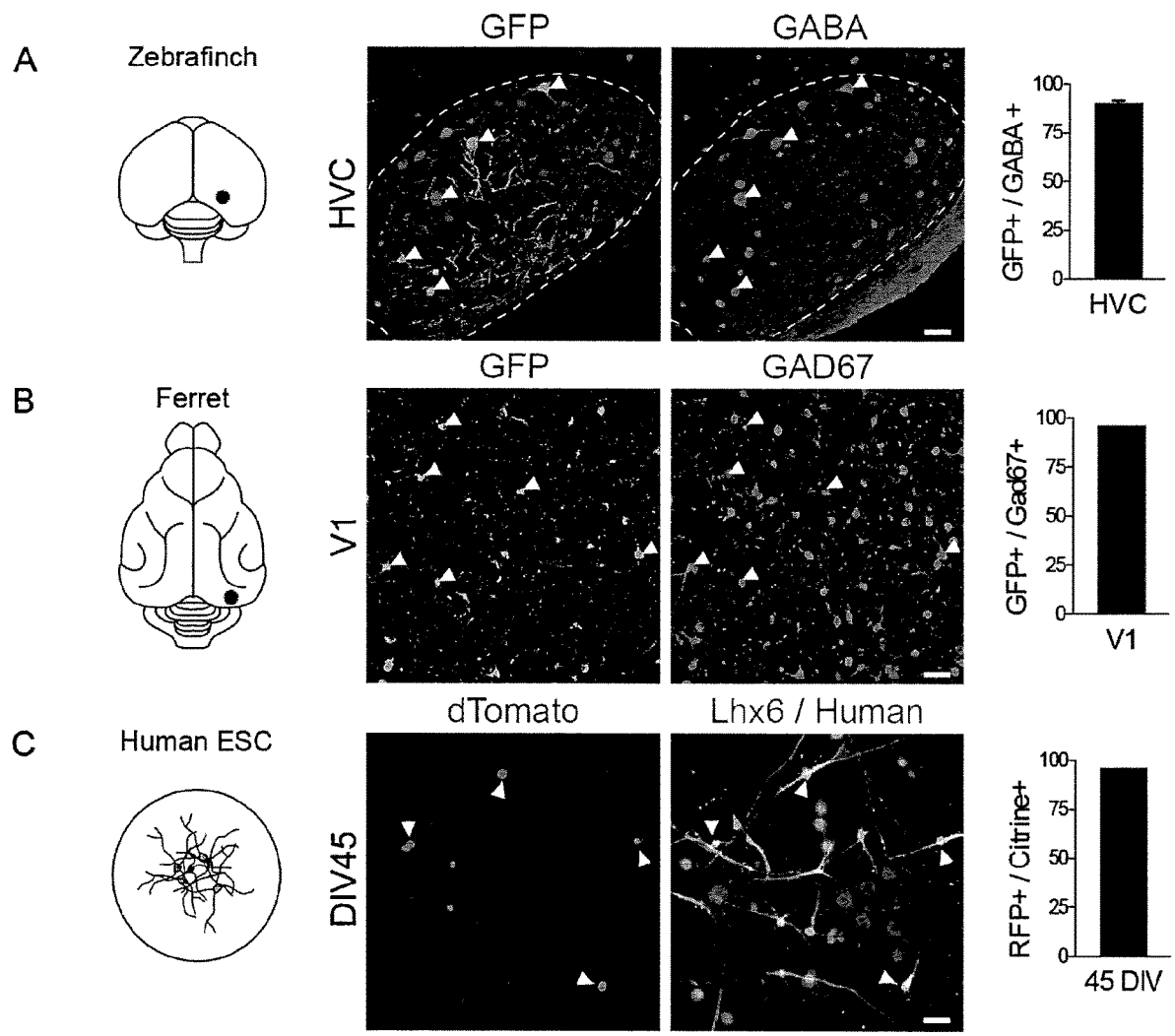
FIG. 3. Both mouse and human I56i shows high specificity for GABAergic interneurons across species.

This Example demonstrates interneuron specificity across species. In connection with this, the high degree of conservation of the genomic sequence of mI56i across species is suggestive of an important and conserved role in gene regulation across species. To analyze this, adult zebra finches and juvenile ferrets were injected with rAAV-mI56i-GFP. Similar to the results obtained in mice, immunostaining revealed a sparse but intense labeling in the injected regions, with the majority of infected cells (~95%) co-localized with pan-interneuron markers GABA or Gad67 (FIG. 3A,B). To further confirm these data, Lhx6-Citrine Human Embryonic Stem Cells (hESC) derived interneurons (where the expression of the green fluorescent reporter Citrine is restricted to interneurons) were infected with the another version of the virus containing the humanized version of the I56i enhancer (rAAV-hI56i-dTomato). Immunostaining revealed the majority of dTomato+ infected were Citrine+(~94%—FIG. 3C). These data thus demonstrate that the specificity of the I56i enhancer is retained in all the species tested. Moreover, it is demonstrated that rAAV-hI56i-dTomato labels human GABAergic interneurons with what is believed to be unprecedented specificity.

Example 4

This Example demonstrates functionality of rAAVs of this disclosure in adult mice. In particular, the enhancer approach was modified such that it is linked with Gq-DREADD expression. To model use of rAAV-hI56i-Gq-DREADD to focally restore E/I balance in epileptic patients an rAAV expressing a HA-tagged version of the Gq-DREADD of SEQ ID NO:1, followed by the red fluorescent reporter dTomato under the control of the human Dlx enhancer element hI56i (rAAV-hI56i-Gq-DREADD) was generated. First, whether the expression of a larger construct could influence the targeting specificity of the hI56i enhancer was tested. Immunofluorescence analyses of adult mice injected with the rAAV-hI56i-Gq-DREADD revealed that the majority of infected cells co-localized with GABA (~92%—data not shown). The Gq-DREADD was located at the membrane of the infected cells (FIG. 4A), which is consistent with expression of a functional receptor. In addition, current clamp recordings from acute brain slices of injected animals showed all dTomato-expressing cells had firing patterns corresponding to fast spiking (FS) and low-threshold spiking (LTS) neurons (FIG. 4E). These two cell types are well known to correspond to parvalbumin and somatostatin interneurons, which represent the majority of interneurons populating in this layer (Rudy, B., et al. Three groups of interneurons account for nearly 100% of neocortical GABAergic neurons. *Devel Neurobio* 71, 45-61 (2011)). Post-hoc histological examination of morphologically recovered cells confirmed their interneuronal nature (round soma, non-spiny dendrites and dense local axon—FIG. 4D). These data confirm that the rAAV-hI56i-Gq-DREADD-dTomato drives the expression of the Gq-DREADD exclusively at the membrane of GABAergic interneurons. The functionality of the Gq-DREADD was then tested. Upon bath application of CNO (500 nM), all infected interneurons with expression of the Gq-DREADD, as indicated by mTomato expression, showed membrane potential depolarization within less than a minute. Although CNO application depolarized in a similar range and could elicit action potential in all interneurons examined, low-threshold spiking cells (LTS) showed the most dramatic increase in firing (FIG. 4B,C,F). Voltage clamp recordings of pyramidal cells (in the vicinity of the Gq-DREADD expressing interneurons, which while likely infected showed no indication of G1-DREADD expression) showed an increase in IPSCs upon CNO application for cells within, but not outside the injection site (FIG. 4G-I).

Taken together these data demonstrate that the rAAV-hI56i-Gq-DREADD selectively drives expression of Gq-DREADD in interneurons, and that administration of a Gq-DREADD agonist leads to a local increase of interneuron activity, resulting in an overall increase of inhibitory drive on the pyramidal cells specifically at the site of injection. These results thus show that rAAV-hI56i-Gq-DREADD allows specific and functional expression of Gq-DREADD and that Gq-DREADD agonist treatment effectively increases the activity of GABAergic interneurons, resulting in a functional, local and specific increase of inhibition in the neighboring excitatory neurons.

While the disclosure has been particularly shown and described with reference to specific embodiments, it should be understood by those having skill in the art that various changes in form and detail may be made therein without departing from the spirit and scope of the present disclosure as disclosed herein.

---

SEQUENCE LISTING

```
<160> NUMBER OF SEQ ID NOS: 2

<210> SEQ ID NO 1
<211> LENGTH: 590
<212> TYPE: PRT
<213> ORGANISM: artificial sequence
<220> FEATURE:
<223> OTHER INFORMATION: Derivative of the amino-acid sequence of the
      human muscarinic acetylcholine receptor M3 in which the tyrosine
      in position 149 is replaced by a cysteine and the arginine in
      position 239 is replaced by a glycine

<400> SEQUENCE: 1

Met Thr Leu His Asn Asn Ser Thr Thr Ser Pro Leu Phe Pro Asn Ile
1               5                   10                  15

Ser Ser Ser Trp Ile His Ser Pro Ser Asp Ala Gly Leu Pro Pro Gly
            20                  25                  30

Thr Val Thr His Phe Gly Ser Tyr Asn Val Ser Arg Ala Ala Gly Asn
        35                  40                  45

Phe Ser Ser Pro Asp Gly Thr Thr Asp Asp Pro Leu Gly Gly His Thr
    50                  55                  60

Val Trp Gln Val Val Phe Ile Ala Phe Leu Thr Gly Ile Leu Ala Leu
65                  70                  75                  80

Val Thr Ile Ile Gly Asn Ile Leu Val Ile Val Ser Phe Lys Val Asn
                85                  90                  95

Lys Gln Leu Lys Thr Val Asn Asn Tyr Phe Leu Leu Ser Leu Ala Cys
            100                 105                 110

Ala Asp Leu Ile Ile Gly Val Ile Ser Met Asn Leu Phe Thr Thr Tyr
        115                 120                 125

Ile Ile Met Asn Arg Trp Ala Leu Gly Asn Leu Ala Cys Asp Leu Trp
    130                 135                 140

Leu Ala Ile Asp Cys Val Ala Ser Asn Ala Ser Val Met Asn Leu Leu
145                 150                 155                 160

Val Ile Ser Phe Asp Arg Tyr Phe Ser Ile Thr Arg Pro Leu Thr Tyr
                165                 170                 175
```

Arg Ala Lys Arg Thr Thr Lys Arg Ala Gly Val Met Ile Gly Leu Ala
                180                 185                 190

Trp Val Ile Ser Phe Val Leu Trp Ala Pro Ala Ile Leu Phe Trp Gln
            195                 200                 205

Tyr Phe Val Gly Lys Arg Thr Val Pro Pro Gly Glu Cys Phe Ile Gln
        210                 215                 220

Phe Leu Ser Glu Pro Thr Ile Thr Phe Gly Thr Ala Ile Ala Gly Phe
225                 230                 235                 240

Tyr Met Pro Val Thr Ile Met Thr Ile Leu Tyr Trp Arg Ile Tyr Lys
                245                 250                 255

Glu Thr Glu Lys Arg Thr Lys Glu Leu Ala Gly Leu Gln Ala Ser Gly
            260                 265                 270

Thr Glu Ala Glu Thr Glu Asn Phe Val His Pro Thr Gly Ser Ser Arg
        275                 280                 285

Ser Cys Ser Ser Tyr Glu Leu Gln Gln Gln Ser Met Lys Arg Ser Asn
    290                 295                 300

Arg Arg Lys Tyr Gly Arg Cys His Phe Trp Phe Thr Thr Lys Ser Trp
305                 310                 315                 320

Lys Pro Ser Ser Glu Gln Met Asp Gln Asp His Ser Ser Ser Asp Ser
                325                 330                 335

Trp Asn Asn Asn Asp Ala Ala Ala Ser Leu Glu Asn Ser Ala Ser Ser
            340                 345                 350

Asp Glu Glu Asp Ile Gly Ser Glu Thr Arg Ala Ile Tyr Ser Ile Val
        355                 360                 365

Leu Lys Leu Pro Gly His Ser Thr Ile Leu Asn Ser Thr Lys Leu Pro
    370                 375                 380

Ser Ser Asp Asn Leu Gln Val Pro Glu Glu Glu Leu Gly Met Val Asp
385                 390                 395                 400

Leu Glu Arg Lys Ala Asp Lys Leu Gln Ala Gln Lys Ser Val Asp Asp
                405                 410                 415

Gly Gly Ser Phe Pro Lys Ser Phe Ser Lys Leu Pro Ile Gln Leu Glu
            420                 425                 430

Ser Ala Val Asp Thr Ala Lys Thr Ser Asp Val Asn Ser Ser Val Gly
        435                 440                 445

Lys Ser Thr Ala Thr Leu Pro Leu Ser Phe Lys Glu Ala Thr Leu Ala
    450                 455                 460

Lys Arg Phe Ala Leu Lys Thr Arg Ser Gln Ile Thr Lys Arg Lys Arg
465                 470                 475                 480

Met Ser Leu Val Lys Glu Lys Lys Ala Ala Gln Thr Leu Ser Ala Ile
                485                 490                 495

Leu Leu Ala Phe Ile Ile Thr Trp Thr Pro Tyr Asn Ile Met Val Leu
            500                 505                 510

Val Asn Thr Phe Cys Asp Ser Cys Ile Pro Lys Thr Phe Trp Asn Leu
        515                 520                 525

Gly Tyr Trp Leu Cys Tyr Ile Asn Ser Thr Val Asn Pro Val Cys Tyr
    530                 535                 540

Ala Leu Cys Asn Lys Thr Phe Arg Thr Thr Phe Lys Met Leu Leu Leu
545                 550                 555                 560

Cys Gln Cys Asp Lys Lys Lys Arg Arg Lys Gln Gln Tyr Gln Gln Arg
                565                 570                 575

Gln Ser Val Ile Phe His Lys Arg Ala Pro Glu Gln Ala Leu
            580                 585                 590

```
<210> SEQ ID NO 2
<211> LENGTH: 297
<212> TYPE: DNA
<213> ORGANISM: human

<400> SEQUENCE: 2
caggatcaat tctgaacaaa gcctccagct gcagtgccat ccaatttgaa gcagacattg      60
gggacaattt aaggttttta tccacaagaa ggttttttc cattctctta aatgcagcca     120
taattagagt aattttcat gtagcccgct gattacagcg tttttaccgt caaagataat     180
tacctgtaat tttcttccac ttttaatact aaaaagccat ctttatttag attcaggaac    240
aggaaaggcg aaacaaaaga gggaaattat tctgttattc atacacaaat tgcagag       297
```

What is claimed is:

1. A method for prophylaxis and/or therapy for seizures in an individual mammal in need thereof, the method comprising administering with a stereotactic injection into the somatosensory cortex, hippocampus and/or striatum of the mammal's brain a recombinant adeno-associated virus (rAAV) comprising a sequence encoding a I56i enhancer and a sequence encoding hM3Dq modified muscarinic receptor (Gq-DREADD) such that neurons of brain of the individual mammal comprise the I56i enhancer sequence that is operably linked to the sequence encoding the Gq-DREADD, wherein the Gq-DREADD is only expressed in adult GABA-ergic interneurons, and subsequently administering to the individual an effective amount of clozapine-N4-oxide (CNO), wherein one or more seizures are inhibited or prevented.

2. The method of claim 1, wherein the individual is experiencing a seizure at time of the administering the CNO and wherein the severity of the seizure is reduced subsequent to the administering.

3. The method of claim 1, wherein the seizure is selected from a partial seizure or a generalized seizure.

4. The method of claim 1, wherein the individual mammal has, is suspected of having, or has been diagnosed with epilepsy.

5. The method of claim 1, wherein the individual mammal has been diagnosed with pharmaco-resistant epilepsy.

* * * * *